US010415179B2

(12) United States Patent
Vinatoru et al.

(10) Patent No.: US 10,415,179 B2
(45) Date of Patent: Sep. 17, 2019

(54) METHOD FOR PRODUCING ANTIMICROBIAL YARNS AND FABRICS BY NANOPARTICLE IMPREGNATION (71) Applicant: COVENTRY UNIVERSITY, Coventry, Warwickshire (GB)

(72) Inventors: Mircea Vinatoru, Coventry (GB); Timothy James Mason, Coventry (GB); Jamie Anthony Beddow, Coventry (GB)

(73) Assignee: Paul G. McClory, Oxon (GB)

( * ) Notice: Subject to any disclaimer, the term of this patent is extended or adjusted under 35 U.S.C. 154(b) by 165 days.

(21) Appl. No.: 15/532,676

(22) PCT Filed: Dec. 3, 2015

(86) PCT No.: PCT/GB2015/053701
§ 371 (c)(1),
(2) Date: Jun. 2, 2017

(87) PCT Pub. No.: WO2016/087864
PCT Pub. Date: Jun. 9, 2016

(65) Prior Publication Data
US 2017/0356127 A1    Dec. 14, 2017

(30) Foreign Application Priority Data
Dec. 3, 2014  (GB) .................................. 1421497.7

(51) Int. Cl.
D06M 16/00    (2006.01)
D06M 10/00    (2006.01)
(Continued)

(52) U.S. Cl.
CPC ............ *D06M 16/00* (2013.01); *A01N 25/10* (2013.01); *A01N 37/02* (2013.01); *A01N 59/20* (2013.01);
(Continued)

(58) Field of Classification Search
None
See application file for complete search history.

(56) References Cited

U.S. PATENT DOCUMENTS

2009/0098033 A1    4/2009  Lian et al.
2011/0097957 A1    4/2011  Gedanken et al.
2011/0135846 A1    6/2011  Seino et al.

FOREIGN PATENT DOCUMENTS

CN    102691204    9/2012
CN    103194891    7/2013
(Continued)

OTHER PUBLICATIONS

International Search Report and Written Opinion for PCT/GB2015/053701, dated Feb. 16, 2016.
(Continued)

*Primary Examiner* — Shamim Ahmed
*Assistant Examiner* — Bradford M Gates
(74) *Attorney, Agent, or Firm* — Wenderoth, Lind & Ponack, L.L.P.

(57) ABSTRACT

The invention relates to a method for producing an antimicrobial fabric or yarn, said method comprising the steps of immersing a fabric or yarn in an aqueous solution of a metal salt while simultaneously subjecting said solution to ultrasonic radiation; and removing the fabric or yarn from said solution and subsequently converting the metal salt in situ in the fabric or yarn into metal oxide nanoparticles, preferably via chemical and heat treatment. Fabrics and yarns obtained or obtainable by such method are also provided. In a further aspect the invention provides an apparatus for performing such method.

21 Claims, 4 Drawing Sheets (51) Int. Cl.
| | |
|---|---|
| D06M 10/02 | (2006.01) |
| D06M 10/06 | (2006.01) |
| D06M 10/08 | (2006.01) |
| D06M 11/42 | (2006.01) |
| D06M 11/44 | (2006.01) |
| D06B 3/04 | (2006.01) |
| D06B 3/10 | (2006.01) |
| D06B 13/00 | (2006.01) |
| A01N 25/10 | (2006.01) |
| A01N 37/02 | (2006.01) |
| A01N 59/20 | (2006.01) |
| D06M 11/07 | (2006.01) |
| D06M 11/51 | (2006.01) |
| D06M 11/84 | (2006.01) |
| D06M 13/188 | (2006.01) |
| D06M 13/52 | (2006.01) |
| D06B 3/20 | (2006.01) |
| D02G 3/44 | (2006.01) |
| D06M 101/06 | (2006.01) |

(52) U.S. Cl.
CPC .............. *D02G 3/449* (2013.01); *D06B 3/04* (2013.01); *D06B 3/10* (2013.01); *D06B 3/208* (2013.01); *D06B 13/00* (2013.01); *D06M 10/003* (2013.01); *D06M 10/02* (2013.01); *D06M 10/06* (2013.01); *D06M 10/08* (2013.01); *D06M 11/07* (2013.01); *D06M 11/42* (2013.01); *D06M 11/44* (2013.01); *D06M 11/51* (2013.01); *D06M 11/84* (2013.01); *D06M 13/188* (2013.01); *D06M 13/52* (2013.01); *D06M 2101/06* (2013.01)

(56) References Cited

FOREIGN PATENT DOCUMENTS

| WO | 2010/001386 | 1/2010 |
| WO | 2014/130940 | 8/2014 |
| WO | 2014/181329 | 11/2014 |
| WO | 2015/040435 | 3/2015 |

OTHER PUBLICATIONS

Li et al.; "Microwave Assisted Fabrication of Nano-ZnO Assembled Cotton Fibers with Excellent UV Blocking Property and Waterwash Durability"; Fibers and Polymers; vol. 13; No. 2; 2012; pp. 185-190.

Gouda et al.; "Preparation and Characterization of Some Nanometal Oxides Using Microwave Technique and Their Application to Cotton Fabrics"; Journal of Nanomaterials; vol. 2015; 2015; pp. 1-9.

Abramov et al.; "Pilot scale sonochemical coating of nanoparticles onto textiles to produce biocidal fabrics"; Surface & Coatings Technology; vol. 204; 2009; pp. 718-722.

Beddow et al.; "Sonochemical coating of textile fabrics with antibacterial nanoparticles"; AIP Conference Proceedings; vol. 1433; 2012; pp. 400.

Abramova et al.; "A sonochemical technology for coating of textiles with antibacterail nanoparticles and equipment for its implementation"; Material Letters; vol. 96; 2013; pp. 121-124.

Singh et al.; "Evaluation of Antibacterial Activity of ZnO Nanoparticles Coated Sonochemically onto Textile Fabrics"; Journal of Microbiology, Biotechnology and Food Services; vol. 2; No. 1; 2012; pp. 106-120.

Faheem Uddin; "Environmental Concerns in Antimicrobial Finishing of Textiles"; International Journal of Textile Science; vol. 3; No. 1A; 2014; pp. 15-20.

Perelshtein et al.; "Chitosan and chitosan-ZnO based complex nanoparticles: formation, characterization, and antibacterial activity"; Journal of Materials Chemistry B; vol. 1; 2013; pp. 1968-1976.

Perelshtein et al.; "Enzymatic pre-treatment as a means of enhancing the antibacterial activity and stability of ZnO nanoparticles sonochemically coated on cotton fabrics"; Journal of Materials Chemistry; vol. 22; 2012; pp. 10736-10742.

Perelshtein et al.; "The sonochemical coating of cotton withstands 65 washing cycles at hospital washing standards and reatains its antibacterial properties"; Cellulose; vol. 20; 2013; 7 pages.

Perelshtein et al.; "Antibacterial Properties of an In Situ Generated and Simultaneously Deposited Nanocrystalline ZnO on Fabrics"; ACS Applied Materials & Interfaces; vol. 1; No. 2; 2009; pp. 361-366.

Perelshtein et al.; "Ultrasound Radiation as a "Throwing Stones" Technique for the Production of Antibacterial Nanocomposite Textiles"; ACS Applied Materials & Interfaces; vol. 2; No. 7; 2010; pp. 1999-2004.

Perelshtein et al.; "CuO-cotton nanocomposite: Formation, morphology, and antibacterial activity"; Surface & Coatings Technology; vol. 204; 2009; pp. 54-57.

METHOD FOR PRODUCING ANTIMICROBIAL YARNS AND FABRICS BY NANOPARTICLE IMPREGNATION

The present invention relates to a method of treating fabrics, fibres and yarns whereby to impart antimicrobial (e.g. antifungal) properties. In particular, it relates to a method and apparatus for producing antimicrobial fabrics, fibres and yarns.

Despite advances in modern medical techniques, microbial infections remain a major problem, particularly in the form of hospital-acquired ("nosocomial") infections. Recent studies estimate that in the United States and Europe between 5 and 15% of hospital patients acquire an infection during their hospital stay. This not only gives rise to additional undesirable costs and the burden of additional treatment for health services, but also causes or contributes to deaths which should otherwise be avoidable.

A number of strategies are currently employed to halt the spread of infections in environments where sterile conditions are desired, e.g. in hospitals. One such strategy is the development of fabrics having antimicrobial properties. These may suitably be employed in fabric articles, including clothing such as hospital uniforms and surgical garments, in bed linen such as pillows and bed sheets, and in dressings such as bandages. This helps to prevent or hinder the colonisation of such articles by bacteria and other pathogenic microorganisms and therefore reduces the probability of infections being transmitted by this route. Antimicrobial fabrics may also find application in other environments where microbial contamination is undesirable, such as in biochemical, microbiological and forensic laboratories. Antimicrobial fabrics may also find application in other non-clinical settings such as hotels, nurseries and schools, restaurants, aircraft (e.g. in aircraft seats and headrests), and other locations where it is desirable to control or prevent the spread of infection.

Certain metals and metal oxides are known to possess antimicrobial properties. Among these, silver and silver oxide ($Ag_2O$), are perhaps the best known. Many metals and metal oxides are widely available and relatively cheap and thus it is desirable to develop an efficient method of impregnating fabrics with these materials to impart antimicrobial properties.

Previous efforts to develop a method of producing antimicrobial fabrics are described in WO 2010/001386 A1 (Gedanken et al.) and in Abramov et al., Surface & Coatings Technology 204 (2009) 718-722. Such methods employ ultrasound in order to assist in the formation and coating of metal oxide nanoparticles onto fabrics. A solution of precursor materials is subjected to ultrasonic radiation, which results in the formation of acoustic cavitation bubbles. The rapid collapse of the bubbles creates high localised temperatures and pressures which results in the reaction of the precursors to form solid metal oxide nanoparticles. Collapse of the cavitation bubbles also generates powerful microjets and shockwaves which are capable of projecting the metal oxide nanoparticles thus formed at high speed onto the surface of the fabric.

Previously-described procedures known in the art, such as those of Gedanken et al., suffer from a number of drawbacks. These methods rely on coating fabrics with pre-fabricated metal oxide nanoparticles, i.e. the nanoparticles are formed externally from the fabric and then coated onto it. As such, penetration of the nanoparticles throughout the bulk of the fabric (for example into the body of individual fibres) is poor, with the majority of the nanoparticles being present at the surface of the fabric. Reliance on ultrasonic radiation to blast the metal oxide nanoparticles onto the fabric surface results in significant wastage, with the number of nanoparticles which become attached to the surface representing a small fraction of the total number prepared. Nanoparticles coated onto the surface of the fabric by such methods also tend not to be firmly affixed, and may be easily displaced from the fabric, for example during washing. This can result in a significant loss of antibacterial/antifungal activity after only a single wash, rendering such fabrics unsuitable for further use in preventing the spread of infection.

In conventional methods, control of the concentration and size of metal oxide nanoparticles is difficult, which leads to problems in obtaining a reproducible and uniform distribution of nanoparticles on the fabric surface. Long periods of exposure to the nanoparticle-containing solution and to ultrasonic irradiation (approximately 1 hour or more) are also required to achieve a sufficient nanoparticle coating of the fabric, i.e. at a level which can confer adequate antimicrobial activity. These factors limit the utility of such methods, particularly where it is desired to produce antimicrobial fabric quickly and in bulk.

It is therefore desirable to provide an improved method which overcomes these drawbacks. The present inventors have now found that, instead of using ultrasound to load a fabric with pre-fabricated nanoparticles of a metal oxide, a significantly increased and/or more uniform loading of the metal oxide can be achieved by first immersing (e.g. soaking) the fabric in an aqueous solution of one or more metal salts whilst subjecting the solution to ultrasonication. The metal salt thus loaded into the fabric may then be converted in situ into metal oxide nanoparticles via subsequent chemical and heat treatments. Significantly, a high level of loading of the metal oxide nanoparticles may be achieved in as little time as 3 to 5 minutes, representing a marked improvement over conventional methods in which an ultrasonication time of about 1 hour is required to achieve appreciable nanoparticle loadings.

The method of the invention offers a number of further advantages over conventional methods. Fabrics treated according to this method achieve a substantially uniform loading of metal salt, thus providing a substantially uniform distribution of metal oxide nanoparticles in the finished article following subsequent chemical and heat treatment. By loading the fabric with a metal salt from a solution before the conversion of the metal salt to metal oxide nanoparticles, penetration of the metal salt throughout the structure of the fabric is achieved. This results in the formation of nanoparticles of the metal oxide on both interior and exterior portions of the fabric so increasing its antimicrobial activity.

Nanoparticles of metal oxides produced in situ according to the method of the invention adhere more securely to the fabric and show a reduced tendency to dissolve or leach out over time. The nanoparticles also show a high degree of uniformity in size, which can readily be controlled, for example by appropriate selection of metal salt concentration and/or immersion times to achieve a desired size of nanoparticle (e.g. the higher the concentration, the larger the size of the nanoparticles). In this way, antimicrobial properties can be tailored according to the specific needs of the end user.

In one aspect the present invention thus provides a method for producing an antimicrobial fabric, said method comprising the steps of:
(i) immersing a fabric in an aqueous solution of a metal salt whilst simultaneously subjecting said solution to ultrasonic radiation; and (ii) removing the fabric from said solution and subsequently converting the metal salt in situ in the fabric into metal oxide nanoparticles.

Whilst the method of the invention is described herein primarily in the context of the treatment of a finished fabric or textile, it will be appreciated that the methods may also be employed to treat any component of the fabric or textile before this is woven and/or knitted to produce the finished product. For example, the method may be performed on fibres or yarns comprising interlocked fibres (e.g. spun, filament or texturized yarns). As will be understood, any discussion herein relating to specific features of a method for treating a fabric are equally applicable to methods for treating fibres and yarns.

In a further aspect the invention thus provides a method of treating a fibre or yarn whereby to impart antimicrobial properties, said method comprising the steps of: immersing said fibre or yarn in an aqueous solution of a metal salt whilst simultaneously subjecting said solution to ultrasonic radiation; removing the fibre or yarn from the aqueous solution and subsequently converting said metal salt in situ in and/or on the fibre or yarn into metal oxide nanoparticles. In this aspect of the invention the resulting treated fibres or yarns may be further processed to produce a woven or knitted fabric. For example, the fibres may be spun or twisted to form yarn which may be woven or knitted to produce a fabric. Alternatively, a treated yarn may be used as an antimicrobial thread, e.g. for stitching together pieces of fabric or other non-fabric materials.

In any of the methods herein described, following production of the metal oxide nanoparticles in situ, the fabric, fibres or yarn will generally be washed and/or dried.

The methods of the invention are suitable for application to fabrics, fibres, and yarns which are capable of absorbing water (particularly hydrophilic materials, such as those which are capable of swelling in water). Fabrics, fibres and yarns comprising naturally-occurring fibres (e.g. cotton, hemp, silk) and semi-synthetic fibres (e.g. rayon) are particularly suitable. Preferably the materials to be treated in accordance with the methods described herein comprise at least one type of naturally-occurring fibre.

The metal salt employed in the methods herein described is desirably a salt of a metal whose oxide has antimicrobial properties. The metal salt employed is therefore preferably a salt of copper, zinc, or magnesium. Although silver can be used, this is generally less preferred due to the grey/black colour of its metal oxide.

Any suitable inorganic or organic salt may be employed provided that this is water-soluble to some degree. Exemplary inorganic salts suitable for use in the method of the invention therefore include the halides (i.e. the fluorides, chlorides, bromides, and iodides, preferably the chlorides), nitrates, nitrites and sulphates of the chosen metal, e.g. copper, zinc or magnesium. Exemplary organic salts include the acetates of the chosen metal, e.g. copper, zinc, or magnesium, and the salts of such metals with propionic and butyric acids. Of the organic salts, the acetates are preferred as these are known to be highly compatible with natural fibres such as cotton.

Optionally the aqueous solution may contain a plurality of different metal salts. The aqueous solution may, for instance, contain two or more salts having a metal in common, such as copper (II) chloride and copper (II) sulphate; two or more salts having different metals but a common ligand, such as copper (II) acetate and zinc acetate; or two or more salts having neither metal nor ligand in common, such as copper (II) acetate and zinc sulphate.

In an embodiment the aqueous solution contains only a single metal salt.

Suitable salts for use in the method of the invention therefore include, but are not limited to: copper (II) sulphate, copper (II) acetate, copper (II) chloride, copper (II) fluoride, copper (II) bromide, copper (II) iodide, copper (II) nitrate, copper (II) nitrite, copper (II) propanoate, copper (II) butanoate, zinc sulphate, zinc acetate, zinc chloride, zinc fluoride, zinc bromide, zinc iodide, zinc nitrate, zinc nitrite, zinc propanoate, zinc butanoate, magnesium sulphate, magnesium acetate, magnesium chloride, magnesium fluoride, magnesium bromide, magnesium iodide, magnesium nitrate, magnesium nitrite, magnesium propanoate, magnesium butanoate, and mixtures thereof.

Preferably the aqueous solution does not contain silver or any salts of silver. Although the antimicrobial properties of silver and silver oxide are well known, silver salts can be problematic to work with. For example, silver nitrate is toxic and corrosive, while silver halides are light-sensitive. Silver oxide is grey/black in colour and can therefore lead to unsightly staining of fabrics. Silver is also relatively expensive. For these reasons it is preferred that the aqueous solution is substantially silver-free, i.e. contains no more than naturally-occurring trace amounts of silver.

In an embodiment the aqueous solution does not contain copper or any salts of copper, as these can also lead to unsightly staining of fabrics (e.g. with a brownish colour).

By suitable selection of the concentration of the metal salt (or salts) in the aqueous solution, it is possible to control the size of the metal oxide nanoparticles which are formed and thus tailor this as desired. As a general rule, lower salt concentrations give rise to smaller nanoparticles and higher salt concentrations give rise to larger nanoparticles. Higher salt concentrations can cause the nanoparticles to be closely grouped within the fabric. At particularly high concentrations, this can give rise to undesirable agglomeration of nanoparticles into a nanocluster (a grouping of particles having an overall size of 500 nm or greater). It is preferable that the metal oxide nanoparticle distribution is uniform and substantially free of nanoclusters. The formation of nanoclusters is undesirable as this reduces the uniformity of the nanoparticle distribution and can lead to a decrease in antimicrobial performance. With this in mind the salt concentration is preferably chosen whereby to minimise the probability of nanocluster formation.

Suitable salt concentrations may readily be determined by those skilled in the art depending on factors such as the nature of the fabric to be treated, the chosen metal salt, the desired amount and size of the metal oxide nanoparticles, etc., but may range from about 0.001 moles per liter (mol/L) to about 0.25 moles per liter, e.g. 0.01 mol/L to 0.25 mol/L, 0.01 mol/L to 0.2 mol/L, 0.01 mol/L to 0.15 mol/L, 0.01 mol/L to 0.1 mol/L, 0.05 mol/L to 0.2 mol/L, 0.05 mol/L to 0.15 mol/L, or 0.5 mol/L to 0.1 mol/L.

Immersion of the fabric in the metal salt solution is accompanied by irradiation with ultrasonic radiation; this may also be referred to as "irradiation", "sonication" or "ultrasonication". The inventors have found that "silent" soaking (i.e. soaking in the absence of ultrasonic radiation) does not give rise to particularly effective impregnation of the fabric by the metal salt solution. "Silent" soaking mainly gives rise to surface deposition of the metal salt with poor penetration into the body of any fibres or yarns in the fabric. By contrast, soaking in conjunction with ultrasonic radiation provides not only a much greater loading of metal salt, but also enables deeper penetration of the salts into the body of the fibres and yarns. A "pre-soaking" step (i.e. a step of silent soaking) prior to subjecting the metal salt solution to ultrasonic radiation may be carried out, however, the inventors have found that this does not generally produce a noticeable difference in loading or penetration. Whilst a pre-soaking step may be performed in the methods herein described, this is not considered to be essential. In one embodiment of the methods herein described, no pre-treatment step in which the fabric, fibre or yarn is immersed or soaked in the metal salt solution prior to ultrasonication is performed.

The use of ultrasound irradiation not only provides improved loading and penetration of the metal salt into the fabric/yarns when compared to "silent" soaking, but also reduces the amount of time required to achieve a given loading compared to known treatment methods. This is especially advantageous for industrial-scale applications where a high rate of production is desirable.

In methods known in the art, such as those described by Gedanken et al., metal oxide nanoparticles are generated by a reaction in situ in a solution of metal salt to which liquid ammonia has been added. Ultrasonication generates cavitation bubbles which collapse, generating high localised temperatures and pressures sufficient to cause reaction between the metal salt and the ammonia and subsequent formation of a metal oxide nanoparticle. However, this results in nanoparticles predominantly being formed in the solution and external to the fabric, and thus relies on the shockwaves generated by the collapse of the cavitation bubbles to propel the nanoparticles onto the fabric. As noted herein, such processes are wasteful as only a small fraction of nanoparticles will be coated onto the fabric. The fabrics generated by such methods also have various drawbacks as noted above (e.g. coating is restricted to the surface of the fabric). In order to avoid the formation of metal oxide nanoparticles in situ in the soaking solution during ultrasonication, which would give rise to wastage and the aforementioned problems, the soaking solution employed in the methods of the present invention is desirably substantially free of any ammonia or ammonia derivatives.

The duration of soaking and sonication may suitably be chosen whereby to achieve a desired level of metal salt loading and to control the nanoparticle size which is ultimately achieved following conversion of the metal salt into the metal oxide. A longer soaking/sonication time gives rise to a larger salt concentration in the fabric and thus a larger average nanoparticle size. A shorter soaking/sonication time gives rise to a lower salt concentration in the fabric and thus a smaller average nanoparticle size. Thus, not only the salt concentration in the soaking solution, but also the soaking/sonication time, may suitably be chosen by the skilled worker in order to optimise the ultimate nanoparticle distribution and size.

Typical durations for the soaking/sonication step may readily be determined by those skilled in the art taking into account factors such as the nature of the fabric/yarns, its size and thickness, etc. For fabrics comprising natural fibres such as cotton, for example, the duration of the soaking/sonication step may generally be about 15 minutes or less, preferably about 10 minutes or less, e.g. about 8 minutes or less. A duration of about 3 to about 8 minutes is especially preferred, e.g. about 5 minutes.

Ultrasonic radiation ("ultrasound") refers to sound with a frequency greater than the upper limit of the typical human hearing range. Ultrasound is thus distinguished from "normal" sound simply by frequency. As used herein, any reference to ultrasonic radiation or ultrasound should be understood as referring to sound with a frequency or at least about 18 kHz. Typically the ultrasound employed may have a frequency of about 18 to about 50 kHz, e.g. about 20 to about 45 or about 20 to about 30 kHz. In an embodiment the frequency is about 25 kHz. In another embodiment the frequency is about 40 kHz.

The acoustic power of the ultrasound may range from about 2 kW to about 12 kW, e.g. about 2.5 kW to about 11 kW, about 2.5 kW to about 5.5 kW, about 2.5 kW to about 6 kW, about 3 kW to about 10 kW, or about 3 kW to about 5 kW. In an embodiment an acoustic power of about 9 kW is employed. In another embodiment an acoustic power of about 5 kW or less is employed. It will be understood that the ultrasonic power employed will be dependent, to some extent, on the duration of the soaking step—it is possible to use a lower power with a higher residence time in the ultrasonic soaking tank, and a higher power with a shorter residence time.

If desired, the metal salt solution may be agitated mechanically at the same time as undergoing sonication. Such agitation may assist in achieving still greater metal salt loading and penetration of the fabric. Suitable means of agitation will be readily determinable by the skilled person and may include, for example, stirring (e.g. by means of a magnetic stirrer) or shaking (e.g. by means of placing any vessel used for the soaking and sonication steps onto a mechanical shaker table). In embodiments such as those described herein where the aqueous metal salt solution is recirculated (e.g. by pumping means), agitation may also be achieved simply by the motion of the solution caused by its recirculation. Agitation is not an essential part of the methods of the invention.

The steps of impregnating the fabric and subjecting the impregnated fabric to ultrasonication are preferably carried out at a temperature of up to about 60° C. The appropriate temperature for impregnation and ultrasonication may depend on the nature of the fabrics, fibre or yarns to be treated and suitable temperatures for any particular materials may readily be determined by those skilled in the art. In an embodiment the steps of impregnating the fabric and subjecting the impregnated fabric to ultrasonication are carried out at ambient temperature, i.e. at a temperature in the range of about 18° C. to about 25° C., e.g. 20° C. to 25° C. Ambient temperature treatment is particularly suited to the treatment of natural fabrics such as cotton.

In one embodiment of the methods herein described, the conductivity of the soaking solution may be monitored during ultrasound treatment. A decrease in conductivity signifies a decrease in the ionic strength of the solution and thus indicates that the metal salt is being absorbed into the fabric. In this way the conductivity measurement can be used to estimate the loading of the fabric.

In one embodiment, the step of impregnating the fabric may involve the step of replenishing lean or 'spent' metal salt solution (i.e. solution which has a reduced concentration of metal salt following its depletion). This may be achieved by replacing this with fresh metal salt solution and/or by the addition of metal salt to the 'spent' solution. In one embodiment treatment of the fabric may be performed in a vessel having both an inlet and an outlet for the soaking solution. Fresh soaking solution (with a metal salt concentration suitable for achieving a target metal salt loading into the fabric) is introduced to the vessel via the inlet. Soaking solution flows through the vessel from the inlet to the outlet at a rate such that a constant volume of soaking solution is present in the vessel at all times. Soaking solution exits the vessel via the outlet. The conductivity of the soaking solution may be measured both at the inlet and at the outlet. Any decrease in conductivity from the inlet to the outlet allows the level of depletion of metal salt in the soaking solution to be estimated. This in turn allows the loading of the fabric with metal salt to be estimated. The soaking solution recovered from the outlet may be recirculated to the inlet, preferably via a receiving or buffer tank in which additional metal salt is added in order to raise the metal salt concentration back to a level equal to that of "fresh" soaking solution (i.e. its initial concentration). In this way a constant concentration of metal salt can be maintained in the soaking solution in the vessel. This is particularly advantageous in the context of a continuous production method.

The monitoring of conductivity thus offers an additional means of controlling the level of metal salt loading in the fabric in the soaking vessel, as the flow rate of soaking solution through the vessel can be increased or decreased in order to achieve a desired loading. Other control means include the residence time of the fabric in the soaking solution—in the case of a continuous process this is dependent on the speed of passage of the fabric through the solution (i.e. the higher the speed of passage, the lower the loading of metal salts into the fabric).

The overall level of metal salt loading in the fabric in the soaking vessel may therefore be controlled according to a number of factors such as the concentration of metal salt in the soaking solution, the flow rate of soaking solution through the vessel (when this is recirculated), the duration of exposure of the fabric to the soaking solution, the duration of ultrasonic radiation, the rate of passage of the fabric through the soaking solution (where a continuous process such as those described herein is employed), etc. For example, for a constant salt concentration in the soaking solution, a higher rate of passage of the fabric through the soaking solution will result in a lower salt loading. For a constant rate of passage through the soaking solution, a lower salt concentration in the soaking solution will result in a lower salt loading. Those skilled in the art may readily determine the appropriate combination of processing parameters, such as those discussed above, which may be required in order to achieve a given salt loading and, in turn, a desired loading of metal oxide nanoparticles in the final product.

Following treatment with the metal salt solution, the fabric is treated in order to transform the metal salt, which has been impregnated into the fabric, into metal oxide nanoparticles. Typically this is achieved by chemical and heat treatment.

Chemical treatment may involve exposure of the impregnated fabric to ammonia. The metal salt and residual water from the soaking solution react with the ammonia to produce a metal-ammonia complex in the fabric. After being exposed to ammonia the fabric is heated, causing the metal-ammonia complex to react and form a metal oxide. Preferably exposure to ammonia occurs at ambient temperature.

Where ammonia is employed, this may be in liquid, solution or gaseous form. Preferably the ammonia is in the form of a gas. The gaseous ammonia may be employed at a pressure slightly higher than atmospheric pressure, e.g. at a pressure of about 1.1 to about 1.5 bar. A pressure of about 1.2 bars is particularly preferred.

The fabric impregnated with the metal salt is desirably exposed to the ammonia for a length of time sufficient to ensure substantially complete reaction between the metal salt and the ammonia. The appropriate exposure time may depend on the nature of the metal salt, the level of salt loading, and/or on the type of fabric undergoing treatment. Suitable exposure times for any given metal salt, salt loading and/or fabric can be determined by the skilled person to ensure substantially complete reaction. For natural fabrics such as cotton, typically an exposure time of about 2 to about 30 minutes is sufficient, preferably about 2 to about 25 minutes, more preferably about 2 to about 10 minutes, e.g. about 3 to about 5 minutes.

The method of the invention is described herein primarily with reference to the use of ammonia. However, primary amines, such as methylamine and/or ethylamine, may be employed in place of ammonia. Ammonia is, however, generally preferred. Amines other than ammonia, methylamine and ethylamine typically form more stable metal-amine complexes, which are more difficult to transform into oxides.

Following exposure to ammonia, the fabric is heated whereby to form the desired metal oxide. As outlined below, the metal-ammonia complex may decompose to form metal oxide, ammonia gas and water vapour. Timing and temperature of heating will depend on factors such as the nature of the metal, the nature, size and thickness of the fabric, etc., but can readily be determined by those skilled in the art. Heating may be carried out a temperature of about 100° C. to about 150° C., e.g. about 120° C. to about 130° C., preferably about 125° C. to about 130° C., particularly preferably 125° C. to 130° C.

The step of heating the fabric will generally be carried out after the step of exposing the fabric to ammonia. Heating of the fabric may be effected in the same vessel where the exposure to ammonia takes place. Optionally, therefore, the vessel used for ammonia treatment may be purged of any unreacted ammonia before the heating step takes place. In a preferred embodiment exposure to ammonia and heat treatment are effected in separate vessels. Where a separate heating vessel or chamber is employed, unreacted ammonia gas may enter the heating chamber together with the fabric. The heating chamber may therefore be equipped with at least one vent for release of unreacted ammonia. Ammonia gas will also be produced (i.e. regenerated) by the heat-induced decomposition of the metal-ammonia complex, as described above. Ammonia gas regenerated in this manner may also escape the heating chamber through the vent (or vents).

Suitable means of heating include microwave (MW) heating (e.g. by means of a single microwave generator or a plurality of microwave generators arranged along a length of the fabric), heated pipes (e.g. steam filled pipes) or heated rolling drums (e.g. steam-filled rolling drums such as those conventionally used in the textile industry and which come into contact with the treated fabric, fibres or yarns), and/or electrical heating. Microwave heating is particularly preferred as this provides substantially uniform heating of the fabric.

Where microwave heating is employed a microwave power of about 2 kW to about 10 kW is preferably used. Microwave frequencies of about 915 MHz to about 2.5 GHz are suitable. In an embodiment, microwave frequencies of about 2.3 to 2.5 GHz, such as about 2.45 GHz are employed.

The duration of heating required in order to effect substantially complete transformation of the metal-ammonia complex into a metal oxide may depend on factors such as the level of metal salt loading in the fabric and the nature of the fabric, as well as the means of heating employed and the temperature reached. Suitable exposure times and temperatures will readily be determined by those skilled in the art.

The steps of exposing the fabric to ammonia and of heating the fabric must be carried out while the fabric is still damp, i.e. while the fabric still contains sufficient residual water from the soaking solution. If the fabric is allowed to dry before the heating step is performed, the conversion of the metal salt or metal-ammonia complex into metal oxide nanoparticles will not occur.

Without wishing to be bound by theory, it is believed that the conversion of the metal salt to metal oxide nanoparticles is achieved via the following sequence of reactions. These are illustrated with reference to zinc and copper acetate, though the skilled worker will appreciate that similar reactions will occur with other salts and with other metals suitable for use in the present method:

$$Zn(OAc)_2 + 2NH_3 + 2H_2O \rightarrow Zn(OH)_2 + 2NH_4OAc \quad (1)$$

$$Cu(OAc)_2 + 2NH_3 + 2H_2O \rightarrow Cu(OH)_2 + 2NH_4OAc \quad (2)$$

$$Zn(OH)_2 + 4NH_3 \leftrightarrows [Zn(NH_3)_4](OH)_2 \quad (3)$$

$$Cu(OH)_2 + 4NH_3 \leftrightarrows [Cu(NH_3)_4](OH)_2 \quad (4)$$

$$[Zn(NH_3)_4](OH)_2 \xrightarrow{\Delta} ZnO + H_2O + 4NH_3(gas) \quad (5)$$

$$[Cu(NH_3)_4](OH)_2 \xrightarrow{\Delta} CuO + H_2O + 4NH_3(gas) \quad (6)$$

The method of the invention may be carried out as either a batch or continuous process. Preferably, this will be a continuous process involving a steady and continual feed of a length of fabric (or fibre or yarn) through a soaking solution which is subjected to ultrasonic radiation, and subsequently through a region where reaction with ammonia may take place. The rate of passage of the fabric through the soaking solution may be adjusted to ensure that any given portion of the fabric has a residence time in the soaking solution which is suitable to achieve the desired loading or metal salt, and a residence time in the ammonia reaction region which is suitable to achieve substantially complete reaction.

Following conversion of the impregnated metal salt into metal oxide nanoparticles via the ammonia treatment and heating step, the fabric may optionally be washed and/or dried. This may be desirable, for instance, to remove any excess unreacted metal salt solution or ammonia, for example. Washing will generally be carried out using water at low temperature, preferably at about 40° C. or below, more preferably about 30° C. or below, e.g. about 30° C., and in the absence of any added detergent.

In hospitals and other sterile environments, fabrics such as bed linen, clothing, etc. tend to be autoclaved washed under very aggressive conditions, e.g. in water at about 90° C. using strongly acidic or caustic detergents, in order to kill any bacteria. However, fabrics produced according to the method of the invention possess an inherent antibacterial activity due to the presence of the metal oxide nanoparticles. This removes the need for such aggressive washing conditions. Aggressive washing conditions may in fact be detrimental not only to the structure of the fabric but also in that they can result in dissolution and/or leaching of the metal oxide nanoparticles. Any washing conditions should thus be selected to minimise any dissolution and/or leaching of the metal oxide nanoparticles from the fabric, as this will result in a decrease in antibacterial activity. Consequently, gentle washing conditions are preferred, for example, washing with water at a temperature of about 40° C. or below, preferably about 30° C. or below, e.g. at about 30° C. If a detergent is employed this should be a neutral detergent, preferably a detergent whose pH remains substantially constant throughout any washing cycle employed. Suitable neutral detergents will be known to those skilled in the art.

The term "nanoparticles" as employed herein refers to substantially spherical solid particles having a diameter of up to about 250 nm, preferably between about 10 nm and about 200 nm, e.g. between about 100 nm and about 200 nm, such as between about 150 nm and about 200 nm. Preferably the metal oxide nanoparticles of the invention will be substantially uniform in size, e.g. having a standard deviation of no more than 30 nm, preferably no more than 20 nm, in their diameters.

In order to achieve appreciable levels of antibacterial activity a nanoparticle loading of at least about 0.25 grams per square meter of fabric, preferably at least about 0.4 grams per square meter, e.g. about 0.5 grams per square meter, is desirable. The loading needed to achieve antibacterial activity may, however, vary according to the size of nanoparticles employed and those skilled in the art will be able to determine appropriate loadings for any given nanoparticle size or size distribution.

As discussed, the method of the invention may be performed as a batch or continuous process. In a "batch" process, for example, a discrete piece of fabric to be treated may be completely immersed in the soaking solution and sonicated such that the entire piece of fabric is treated at once. Following removal of soaking solution, the fabric is then exposed to ammonia and heat treatment to form metal oxide nanoparticles in situ in the fabric.

Preferably, however, the method of the invention is performed continuously. In a continuous process a length of fabric may be gradually fed through the soaking solution in a first vessel at a rate which is calibrated such that any individual portion of the fabric undergoes soaking/sonication for a length of time suitable for achieving a desired loading of the metal salt into the fabric. Following passage through the soaking solution the fabric passes into a second vessel where it undergoes treatment with ammonia and heat in order to form nanoparticles. As a first portion of the fabric exits the soaking solution and enters the ammonia treatment vessel, a second portion of the fabric is still passing through the soaking solution. In this way long strands of fibre and large rolls of fabric can be treated without the need to employ an unduly large volume of soaking solution, and a fixed size of vessel can be employed for the soaking of varying lengths of fabric rather than requiring different sizes of vessel for different lengths of fabric.

Continuous processes such as those described above may suitably be carried out using an apparatus which is specifically adapted. In a further aspect the invention therefore provides an apparatus for use in the method of the invention, said apparatus comprising: a first vessel for immersing a fabric in a metal salt solution, said vessel being adapted to provide ultrasound radiation to said solution; a second vessel arranged to receive the fabric or yarn from said first vessel, said second vessel being adapted for the exposure of the fabric or yarn to gaseous ammonia; a source of ammonia gas connected to said second vessel; and heating means for heating the fabric or yarn.

The heating means may, for example, be a microwave generator, heated pipes or heated rollers (e.g. pipes or rollers filled with steam), or an electric heater. In an embodiment the heating means comprises a plurality of microwave generators. The heating means may be comprised in the second vessel or may be separate from the second vessel. In an embodiment the heating means is comprised in a heating chamber which is separate from the second vessel such that the fabric enters the heating chamber after leaving the second vessel. In an embodiment the heating chamber comprises at least one vent for the escape of ammonia gas, such as unreacted ammonia gas from the second vessel and/or ammonia gas generated during heat treatment of a metal-ammonia complex. In an embodiment the heating means comprises a plurality of microwave generators arranged such that these are positioned along a length of any fabric passing through the heating chamber.

The apparatus preferably also comprises components for washing and/or drying the fabric following treatment. For example, this may further comprise one or more washing tanks (e.g. tanks connected to a water supply) and/or a drying cabinet.

Preferably the first vessel comprises a salt solution inlet and a salt solution outlet and is connected to a source of metal salt solution.

In an embodiment the second vessel comprises an ammonia gas inlet and an ammonia gas outlet.

In an embodiment of the apparatus, the second vessel comprises an ammonia gas inlet and a separate heating chamber is provided which has an ammonia gas outlet (e.g. a vent). In this embodiment unreacted ammonia gas from the second vessel may pass into the heating chamber together with the fabric and escape via the ammonia gas outlet.

The optional washing tank preferably comprises at least one fresh water inlet and at least one waste water outlet.

Compression means (e.g. a squeezer) may be positioned between the washing tank and the drying cabinet so that a portion of washing water absorbed into the fabric can be squeezed out before the fabric enters the drying cabinet. The squeezer may take the form of connected rollers through which the fabric passes.

Figure 1:
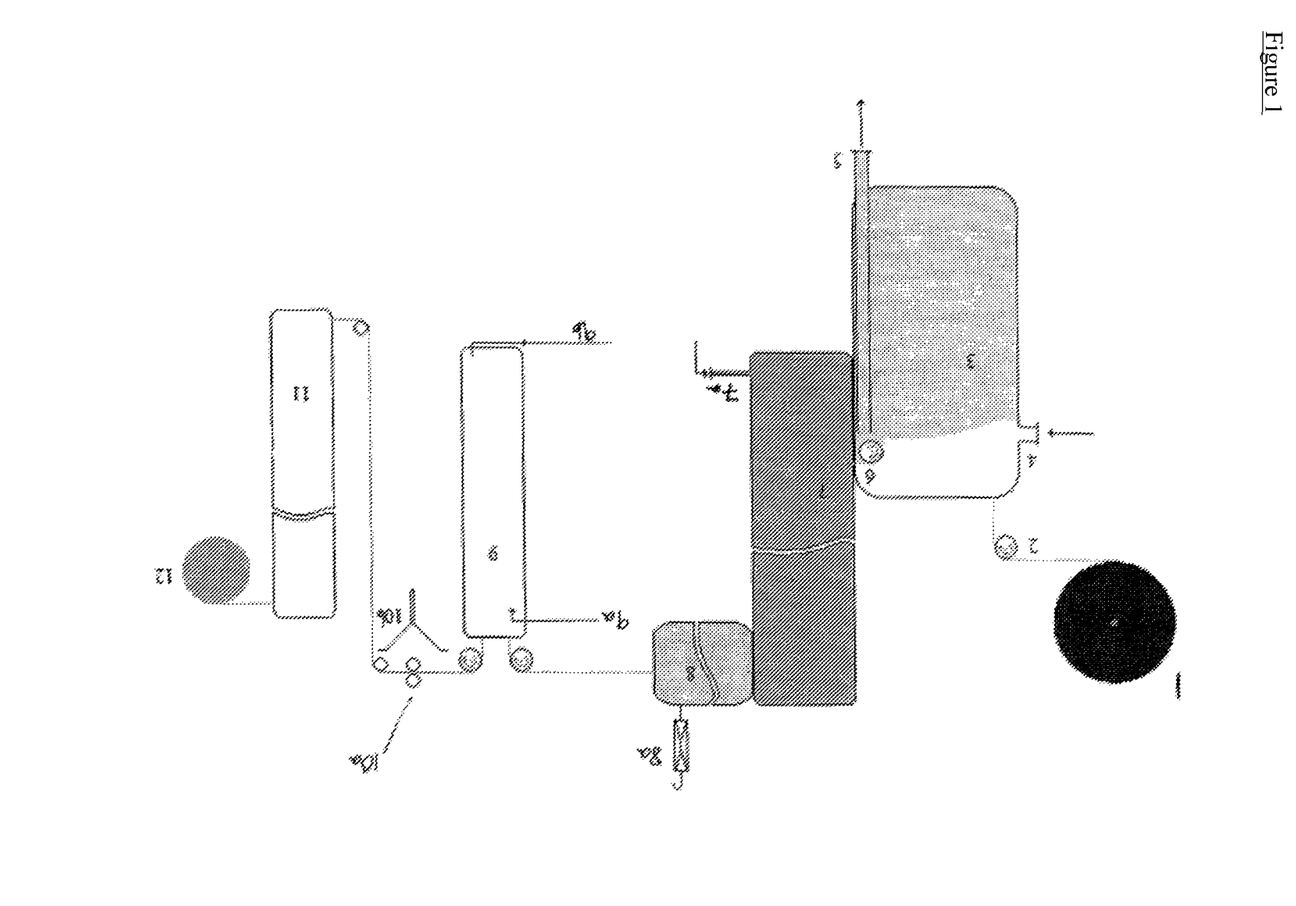
FIG. 1 shows an apparatus according to the invention.

An example of an apparatus according to the invention is shown in attached FIG. 1. Referring to this figure, fabric/yarn from untreated roll 1 is fed via roller 2 into vessel 3. Salt solution enters vessel 3 through inlet 4 and contacts the fabric/yarn, loading a portion of the salt contained therein into the fabric before exiting vessel 3 through outlet 5. The fabric/yarn is conveyed through vessel 3 by mechanical transportation means (e.g. a roller or set of rollers) and exposed to ultrasound generated by ultrasonic transducers. The fabric/yarn exits vessel 3 through aperture 6 which connects to vessel 7. Ammonia gas enters vessel 7 through inlet 7a and contacts the fabric/yarn. The fabric is conveyed through vessel 7 by mechanical transportation means configured to ensure complete exposure of the fabric to the ammonia gas. After exiting vessel 7 the fabric is subjected to heat from heat-generating means in heating chamber 8. Ammonia (including unreacted ammonia gas from vessel 7 and ammonia regenerated by the heat treatment) exits heating chamber 8 through gas vent 8a.

Following exit from heating chamber 8 the fabric is conveyed through washing tank 9 via mechanical transportation means. Fresh water enters the washing tank 9 through an inlet 9a and contacts the fabric before exiting via outlet 9b. The fabric is then conveyed through a squeezer 10a positioned above a drain 10b which collects water squeezed out of the fabric/yarn. Mechanical transportation means conveys the fabric from squeezer 10a into drying cabinet 11. Finally the dried fabric exits the drying cabinet and is wound into treated roll 12.

Figure 2:
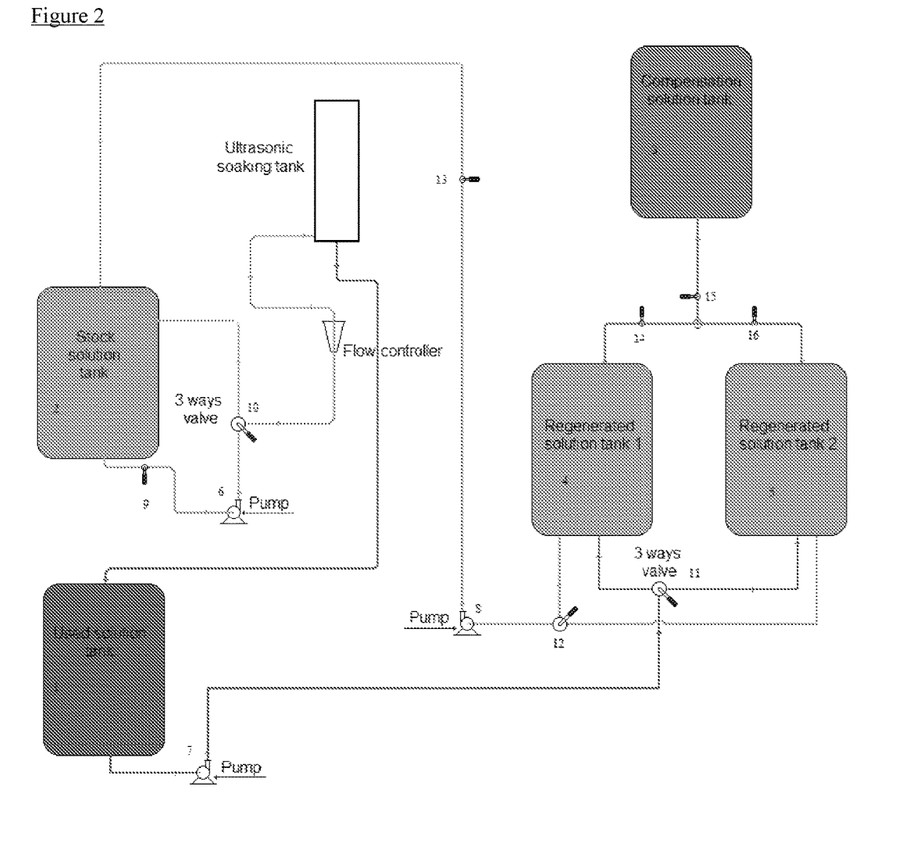
FIG. 2 shows a suitable arrangement of feeding tanks and topping up tanks suitable for recirculation and replenishment of the metal salt soaking solution.

An example of a recirculation circuit which may be employed in the apparatus of the invention in order to allow soaking solution to be continuously circulated and its salt content replenished is shown in attached FIG. 2. Pipe 1a carries lean or "spent" metal salt solution (i.e. solution which has a reduced concentration of metal salt following its depletion) from ultrasonic soaking tank 1b to used solution tank 1. The lean solution is then carried via pipe 1c to one or more of regeneration tanks 4 and 5 where the metal salt concentration is replenished from compensation tank 3 which contains a solution having a higher metal salt concentration. The regenerated solution thus formed is then conveyed via pipe 1d to stock solution tank 2 from where it can flow as required into ultrasonic soaking tank 1b. Pumps 6, 7 and 8, valves 9-16 (including 3-way valves 10 and 11), and flow controller 17 are provided in order to regulate the flow of solutions through the apparatus.

Antibacterial fabrics, fibres or yarns obtained or obtainable by any of the methods described herein form a further aspect of the invention.

The invention will now be described in more detail in the following non-limiting Examples and Figures, in which.

EXAMPLE 1: SOAKING EXPERIMENTS WITH AND WITHOUT SONICATION

Small samples of a cotton fabric were each soaked in a solution of a copper salt. Three different copper salt solutions were employed, each at a concentration of 0.1 moles/L: $CuSO_4.5H_2O$, $CuCl_2.2H_2O$, and $Cu(OAc)_2.H_2O$.

Samples were soaked in the copper salt solutions in the following combinations:
1. $CuSO_4.5H_2O$, 5 minutes' "silent" soaking (no ultrasonication)
2. $CuSO_4.5H_2O$, 5 minutes' soaking with simultaneous ultrasonication
3. $CuCl_2.2H_2O$, 5 minutes' "silent" soaking
4. $CuCl_2.2H_2O$, 5 minutes' soaking with simultaneous ultrasonication
5. $Cu(OAc)_2.H_2O$, 5 minutes' "silent" soaking
6. $Cu(OAc)_2.H_2O$, 5 minutes' soaking with simultaneous ultrasonication
7. $Cu(OAc)_2.H_2O$, continuous "silent" soaking for 2.5 minutes
8. $Cu(OAc)_2.H_2O$, continuous soaking with simultaneous ultrasonication for 2.5 minutes Ultrasonic radiation was provided by an ultrasonic bath, working at 40 kHz and 180 watts power. 2.5 L of salt solution were employed, resulting in an ultrasonic power density of 0.072 $W/cm^3$.

After the end of the soaking period, the samples were removed and dried and the copper content was determined using ICP (inductively coupled plasma atomic absorption spectroscopy).

Figure 3:
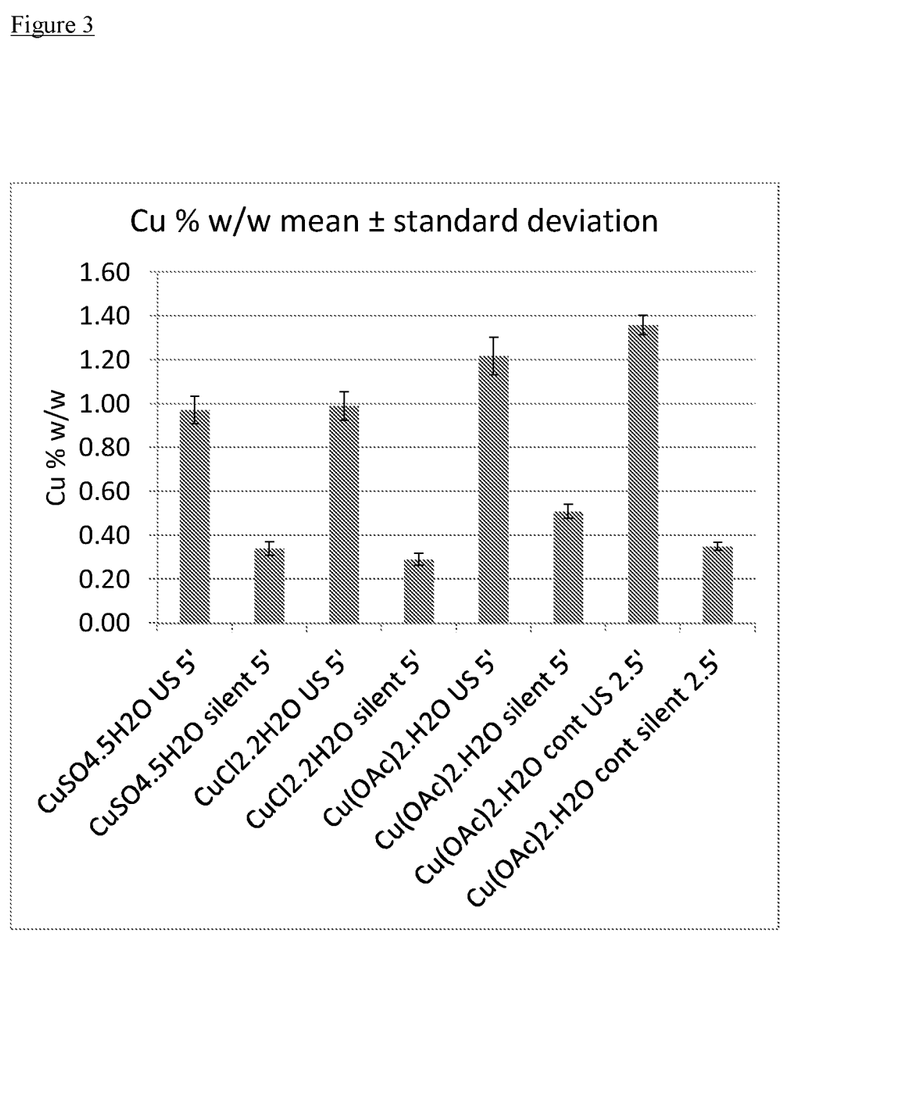
FIG. 3 shows the results of a test comparing metal salt loading into a fabric with and without sonication.

The results are shown in FIG. 3. For all copper salts tested, it was found that soaking with ultrasonication yielded a copper loading between 3 and 5 times greater than "silent" soaking. Of the samples soaked for 5 minutes, which is representative of a typical industrial soaking time, copper acetate demonstrated the greatest loading both under silent and under ultrasonic conditions. This is indicative of the affinity of this salt for natural fibres.

EXAMPLE 2: TREATMENT OF COTTON FABRIC

A sample of cotton fabric was treated using $CuCl_2$ solution and 5 minutes ultrasonication as described above in Example 1. Following this treatment, and whilst still damp, the fabric was exposed to ammonia gas and then heated using microwave radiation of about 2.45 GHz frequency and about 800 W power for about 2 minutes in order to form copper oxide nanoparticles.

Figure 4:
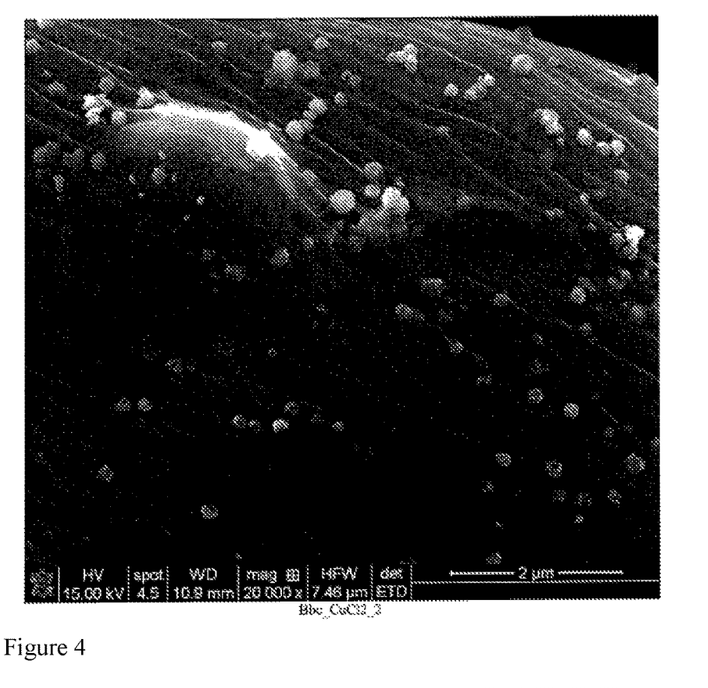
FIGS. 4 and 5 show SEM pictures of a cotton fabric treated according to the method of the invention using $CuCl_2$ as the metal salt.
Figure 5:
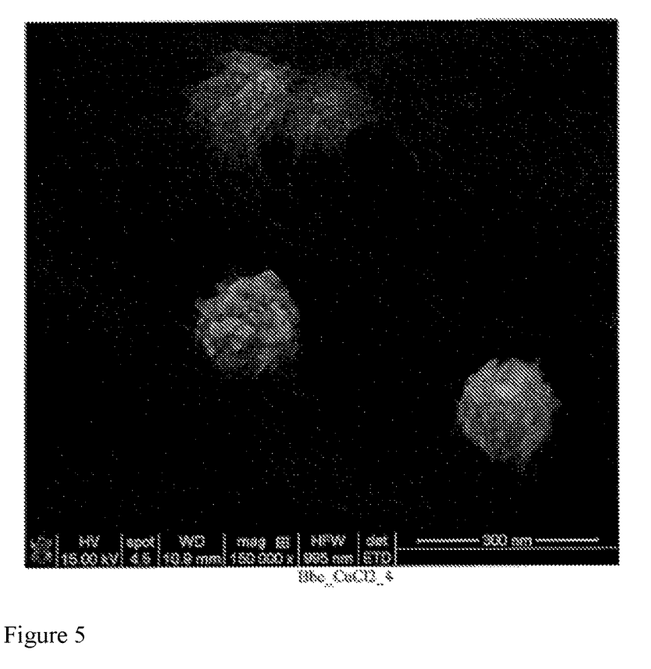

The resulting nanoparticle-impregnated fabric was studied using scanning electron microscopy (SEM), with exemplary results shown in FIGS. 4 and 5. Approximately spherical nanoparticles with a diameter of about 150-200 nm were produced, giving substantially uniform coverage of the fabric.

EXAMPLE 3: ANTIMICROBIAL TEST

Samples of cotton fabrics treated according to the method of the invention were tested against *E. coli* using a simplified absorption test. The samples contained either copper oxide, a copper/zinc oxide combination or zinc oxide nanoparticles. Fabric samples were incubated overnight at 37° C. with a small volume of bacterial suspension containing approx. $2 \times 10^4$ bacteria. After incubation bacteria were washed out of fabrics and plated on nutrient agar plates for overnight incubation and subsequent colony counting. Each live bacterium would result in the growth of one colony.

All of the samples produced >99.9% reduction in cell numbers overnight and zero live bacteria were recovered after incubation, compared to many thousands of bacteria recovered from a plain cotton (untreated) control sample.

The invention claimed is:

1. A method for producing an antimicrobial fabric or yarn, said method comprising the steps of:
   (i) immersing a fabric or yarn in an aqueous solution of a metal salt whilst simultaneously subjecting said solution to ultrasonic radiation; and
   (ii) removing the fabric or yarn from said solution and subsequently converting the metal salt in situ in the fabric or yarn into metal oxide nanoparticles;
   wherein step (ii) comprises exposing the fabric or yarn, whilst still damp, to ammonia or a primary amine in gaseous form; and heating the fabric or yarn.

2. A method according to claim 1, wherein the metal salt is a salt of a metal whose oxide has antimicrobial properties.

3. A method according to claim 1, wherein the metal salt is a salt of copper, zinc or magnesium.

4. A method according to claim 1, wherein the metal salt is a halide, nitrate, nitrite, sulphate, acetate, propanoate or butanoate.

5. A method according to claim 1, wherein the metal salt is selected from the group consisting of copper (II) sulphate, copper (II) acetate, copper (II) chloride, copper (II) fluoride, copper (II) bromide, copper (II) iodide, copper (II) nitrate, copper (II) nitrite, copper (II) propanoate, copper (II) butanoate, zinc sulphate, zinc acetate, zinc chloride, zinc fluoride, zinc bromide, zinc iodide, zinc nitrate, zinc nitrite, zinc propanoate, zinc butanoate, magnesium sulphate, magnesium acetate, magnesium chloride, magnesium fluoride, magnesium bromide, magnesium iodide, magnesium nitrate, magnesium nitrite, magnesium propanoate, magnesium butanoate, and mixtures thereof.

6. A method according to claim 1, wherein the aqueous solution contains only a single metal salt.

7. A method according to claim 1, wherein the aqueous solution contains a plurality of metal salts.

8. A method according to claim 1, wherein the metal salt(s) is/are present in the aqueous solution in an amount of about 0.001 mol/L to about 0.25 mol/L.

9. A method according to claim 1, wherein the aqueous solution is substantially free of ammonia.

10. A method according to claim 1, wherein the duration of ultrasonic radiation is about 15 minutes or less.

11. A method according to claim 1, wherein step (i) is carried out at a temperature of up to about 60° C.

12. A method according to claim 1, wherein the duration of exposure of the fabric or yarn to ammonia or a primary amine is about 25 minutes or less.

13. A method according to claim 1, wherein heating is carried out at a temperature of about 100° C. to about 150° C.

14. A method according to claim 1, wherein heating is carried out by microwave heating or electrical heating.

15. A method according to claim 1 further comprising the following steps:
   (iii) washing the fabric or yarn after step (ii) and, optionally,
   (vi) drying the fabric or yarn.

16. A method according to claim 1, wherein the method is performed as a continuous process.

17. A method according to claim 1, wherein the method is performed as a batch process.

18. A method according to claim 1, wherein the fabric or yarn comprises naturally-occurring or semi-synthetic fibres.

19. A method according to claim 1, wherein the fabric or yarn comprises cotton, hemp, or silk.

20. An apparatus for performing a method as described in claim 1, said apparatus comprising: a first vessel for immersing a fabric in a metal salt solution, said vessel being adapted to provide ultrasound radiation to said solution; a second vessel arranged to receive the fabric or yarn from said first vessel, said second vessel being adapted for the exposure of the fabric or yarn to gaseous ammonia; a source of ammonia gas connected to said second vessel; and heating means for heating the fabric or yarn.

21. An apparatus according to claim 20 further comprising a recirculation circuit adapted to allow a metal salt solution to be continuously circulated through the first vessel whereby to maintain a substantially constant metal salt concentration in the metal salt solution located in the first vessel.

* * * * *